United States Patent
Kim et al.

(10) Patent No.: US 9,522,054 B2
(45) Date of Patent: Dec. 20, 2016

(54) SCANNER FOR ORAL CAVITY

(71) Applicant: THEO DENTAL, Seoul (KR)

(72) Inventors: Jin Hwan Kim, Seoul (KR); Hyun Il Lee, Incheon (KR)

(73) Assignee: THEO DENTAL, Seoul (KR)

( * ) Notice: Subject to any disclaimer, the term of this patent is extended or adjusted under 35 U.S.C. 154(b) by 9 days.

(21) Appl. No.: 14/430,551

(22) PCT Filed: Oct. 31, 2012

(86) PCT No.: PCT/KR2012/009069
§ 371 (c)(1),
(2) Date: Mar. 24, 2015

(87) PCT Pub. No.: WO2014/051196
PCT Pub. Date: Apr. 3, 2014

(65) Prior Publication Data
US 2015/0223916 A1 Aug. 13, 2015

(30) Foreign Application Priority Data
Sep. 25, 2012 (KR) .................. 10-2012-0106580

(51) Int. Cl.
*A61C 9/00* (2006.01)
*A61B 1/247* (2006.01)
(Continued)

(52) U.S. Cl.
CPC ......... *A61C 9/0053* (2013.01); *A61B 1/00172* (2013.01); *A61B 1/24* (2013.01);
(Continued)

(58) Field of Classification Search
CPC ... A61B 5/1079; A61B 5/0088; A61B 5/4547; A61B 1/24; A61B 1/247; A61B 5/0062; A61B 1/00172; A61B 1/00096; A61C 9/0053
See application file for complete search history.

(56) References Cited

U.S. PATENT DOCUMENTS 7,609,875 B2 * 10/2009 Liu .................. A61C 7/00 359/287
2004/0254476 A1 12/2004 Quadling
(Continued)

FOREIGN PATENT DOCUMENTS

KR 10-2005-0122303 A 11/2005
KR 10-0672819 B1 1/2007
(Continued)

OTHER PUBLICATIONS

International Search Report of PCT/KR2012/009069 dated Apr. 29, 2013.
European Search Report for EP application No. 12885649.9.

*Primary Examiner* — Ralph Lewis
(74) *Attorney, Agent, or Firm* — Lee Patent International

(57) ABSTRACT

The invention relates to a scanner for an oral cavity comprising: an optical output unit for outputting a line laser beam; a first optical system for reflecting the line laser beam output from the optical output unit to a scanning target tooth; an optical sensing unit for sensing the line laser beam reflected again by the first optical system after reflected from the scanning target tooth; and a control unit for controlling operations of the optical output unit and the first optical system. The control unit controls the reflection angle and position of the first optical system.

7 Claims, 9 Drawing Sheets

(51) Int. Cl.
    *A61B 5/00*         (2006.01)
    *A61B 5/107*       (2006.01)
    *A61B 1/24*         (2006.01)
    *A61B 1/00*         (2006.01)

(52) U.S. Cl.
    CPC ............ *A61B 1/247* (2013.01); *A61B 5/0062* (2013.01); *A61B 5/0088* (2013.01); *A61B 5/1079* (2013.01); *A61B 5/4547* (2013.01); *A61B 1/00096* (2013.01)

(56) References Cited

U.S. PATENT DOCUMENTS

| | | | |
|---|---|---|---|
| 2006/0269896 A1* | 11/2006 | Liu | A61C 7/00 433/29 |
| 2007/0203663 A1* | 8/2007 | Kopelman | A61B 5/1077 702/127 |
| 2008/0038688 A1* | 2/2008 | Kopelman | A61B 5/1077 433/72 |
| 2011/0080576 A1 | 4/2011 | Thiel | |

FOREIGN PATENT DOCUMENTS

| | | |
|---|---|---|
| KR | 1020090007853 A | 1/2009 |
| KR | 10-2009-0078539 A | 7/2009 |
| KR | 10-2011-0082759 A | 7/2011 |
| KR | 10-2011-0127950 A | 11/2011 |

\* cited by examiner

SCANNER FOR ORAL CAVITY

CROSS-REFERENCE TO RELATED APPLICATION

This application claims the benefit of Korean Patent Application No. 10-2012-0106580 filed on Sep. 25, 2012, and PCT Patent Application No. PCT/KR2012/009069 filed on Oct. 31, 2012, the entire disclosures of which are incorporated herein by reference.

TECHNICAL FIELD

The embodiments described herein pertain generally to a scanner for scanning oral cavity.

BACKGROUND

Generally, in a dental clinic or the like, dental treatment is performed through an impression taking process of taking a plaster cast of patient's teeth. This impression taking process, however, may accompany various problems such as consumption of an impression material, cross-infection, chance of breakage of the fabricated cast, problems in conservation, and so forth.

Conventionally, as a way to investigate the oral health of a patient, there has been widely employed a method of inserting a film in a sheet form into the oral cavity of the patent, fixing the film near an affected area by using the patient's hand or tongue, projecting radioactive rays to the affected area within the oral cavity, and examining the film with an image of the affected area formed thereon.

In such a method, however, since the affected area is measured two-dimensionally from a radiograph through a manual operation, or since this method is CT (Computer Tomography)-dependent, there is a likelihood that an error may occur when measuring a three-dimensional structure on the two-dimensional plane. Further, various problems may also be caused in the clinical aspect because this method exposes the patient to a large quantity of radioactive rays and imposes financial burden on the patient as well as involving a complicated process on the implementation stage.

Meanwhile, in order to form a prosthetic device for restoring a patient's impaired tooth, a plaster cast of the impaired tooth is first fabricated through an impression taking process in the dental clinic, and, then, production of a prosthetic device corresponding to the plaster cast is requested to a dental technician.

According to the conventional prosthetic device production process, however, since treatment data is indirectly acquired from the plaster cast of the tooth to diagnose and measure a current state of the tooth of the patient, it takes great time and effort.

In this regard, Korean Patent Publication No. 10-2009-007853 (entitled "Three-dimensional measure system for the dental prosthesis") describes a measure system for dental prosthesis configured to scan an oral cavity model. The measure system includes an image capturing unit equipped with a camera configured to capture a laser image projected on a measurement target object by using a laser beam, which is irradiated from a laser beam generator, as a light source; an illumination unit provided at one side of the image capturing unit and configured to illuminate toward an irradiation direction of the light source; a linear conveyor unit provided at one side of the illumination unit and configured to move the image capturing unit straightly in one direction by being driven by an electric driving source; a rotary conveyor unit interlocked with the linear conveyor unit and configured to rotate the image capturing unit by being driven to rotate by the electric driving source; and a worktable provided at the rotary conveyor unit in a detachable manner and configured to be moved as one body with the rotary conveyor unit while carrying the measurement target object fixe thereon.

SUMMARY

Example embodiments provide an oral cavity scanner configured to generate a three-dimensional scanning model by scanning teeth in a non-contact manner after inserted into the oral cavity of a dental patient.

Further, the example embodiments also provide an oral cavity scanner capable of increasing an oral cavity scanning velocity and securing an output path for a scanning light source even in an environment where components within the oral cavity scanner are densely arranged.

According to an example embodiment of the present disclosure, there is provided an oral cavity scanner, comprising: an optical output unit configured to output a line laser beam; a first optical system configured to reflect the line laser beam output from the optical output unit to a scanning target tooth; an optical sensing unit configured to sense the line laser beam reflected again by the first optical system after reflected from the scanning target tooth; and a control unit configured to control operations of the optical output unit and the first optical system, wherein the control unit controls a reflection angle and a position of the first optical system.

Especially, the oral cavity scanner may further comprise a second optical system configured to reflect the line laser beam, which is output from the optical output unit in a first traveling direction, in a second traveling direction different from the first traveling direction; and a third optical system configured to reflect the line laser beam, which is reflected from the second optical system, in the first traveling direction; wherein the line laser beam reflected from the third optical system is reflected to the scanning target tooth through the first optical system.

Especially, the oral cavity scanner may further comprise a data processing unit configured to generate three-dimensional data for generating a three-dimensional model of the scanning target tooth based on sensing values output from the optical sensing unit and a value of the reflection angle of the first optical system.

Herein, the data processing unit may generate coordinate data of the scanning target tooth on a plane A-axis based on the value of the reflection angle of the first optical system, and generates height value data for each coordinate of a B-axis line perpendicular to the A-axis.

Especially, the oral cavity scanner may further comprise a two-dimensional imaging device configured to capture a two-dimensional image of the scanning target tooth.

Herein, the control unit may control the two-dimensional imaging device to capture the two-dimensional image of the scanning target tooth before or after the optical output unit outputs the line laser beam.

Herein, the oral cavity scanner may further comprise a data processing unit configured to generate the three-dimensional data for generating the three-dimensional model of the scanning target tooth based on values of electric signals output from the optical sensing unit and the value of the reflection angle of the first optical system, and store the two-dimensional image output from the two-dimensional imaging device while matching the two-dimensional image with the three-dimensional data.

Especially, the oral cavity scanner may comprise a main body in which the optical output unit, the optical sensing unit and the control unit are accommodated; and an insertion body protruded from the main body so as to be inserted into oral cavity, and accommodating therein the first optical system.

Herein, the oral cavity scanner may further comprise a first optical system driving unit provided within the insertion body and configured to slide the first optical system in a forward or backward direction horizontal to an insertion direction of the insertion body into the oral cavity; and a guide member provided within the insertion body and configured to guide the first optical system driving unit to be slid in the forward or backward direction.

Herein, the insertion body may be provided with, at one side thereof, a light transmitting window through which the line laser beam reflected by the first optical system is irradiated to the scanning target tooth.

According to the example embodiments, since the oral cavity scanner can be inserted into the oral cavity of a dental patient and scan teeth of the patient in a non-contact manner, three-dimensional data upon a target tooth can be measured accurately.

According to the example embodiments, by performing the three-dimensional scanning using a light source harmless to a human body, it is possible to conduct scanning of teeth without having adverse effect on user's health.

Further, in accordance with the example embodiments, it is possible to correct a three-dimensional scanning model of a tooth by referring to two-dimensional image data captured within the oral cavity of the dental patent, which is highly convenient.

Moreover, in accordance with the example embodiments, by using a line type light source (i.e., a line laser beam) as a scanning light source, a scanning velocity can be improved, as compared to scanning using a point source. Further, since output positions of the scanning light need not be set to scan individual parts of teeth, a driving unit is not required. That is, since a space for accommodating an additional member for driving an optical output unit and a space for allowing a movement of the optical output unit need not be provided within the oral cavity scanner, the oral cavity scanner can be scaled down and components within the scanner can be arranged highly effectively.

In addition, according to the example embodiments, since a traveling path of the output scanning light source can be changed, it is possible to secure the traveling path of the scanning light source even within the down-sized oral cavity scanner.

MODE FOR CARRYING OUT THE INVENTION

Figure 1:
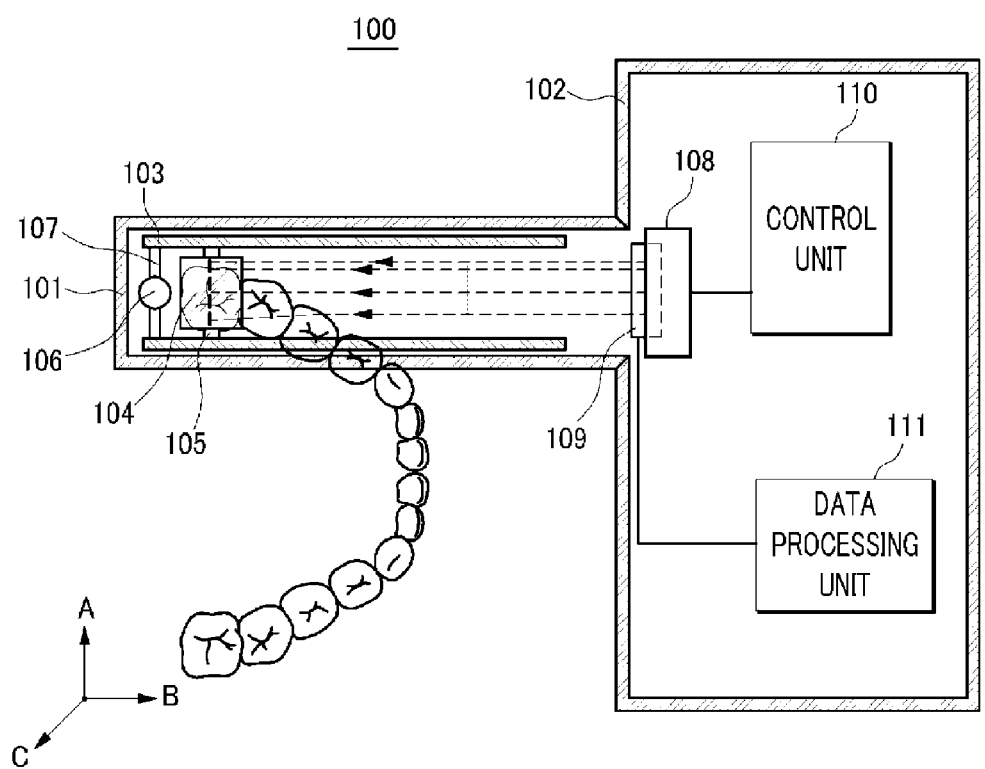
FIG. 1 provides a plane view of an oral cavity scanner in accordance with a first example embodiment of the present disclosure.

Hereinafter, example embodiments will be described in detail so that inventive concept may be readily implemented by those skilled in the art. However, it is to be noted that the present disclosure is not limited to the example embodiments and examples but can be realized in various other ways. In drawings, parts not directly relevant to the description are omitted to enhance the clarity of the drawings, and like reference numerals denote like parts through the whole document.

Through the whole document, the terms "connected to" or "coupled to" are used to designate a connection or coupling of one element to another element and include both a case where an element is "directly connected or coupled to" another element and a case where an element is "electronically connected or coupled to" another element via still another element. Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

FIG. 1 is a plane view of an oral cavity scanner in accordance with a first example embodiment of the present disclosure.

Figure 2:
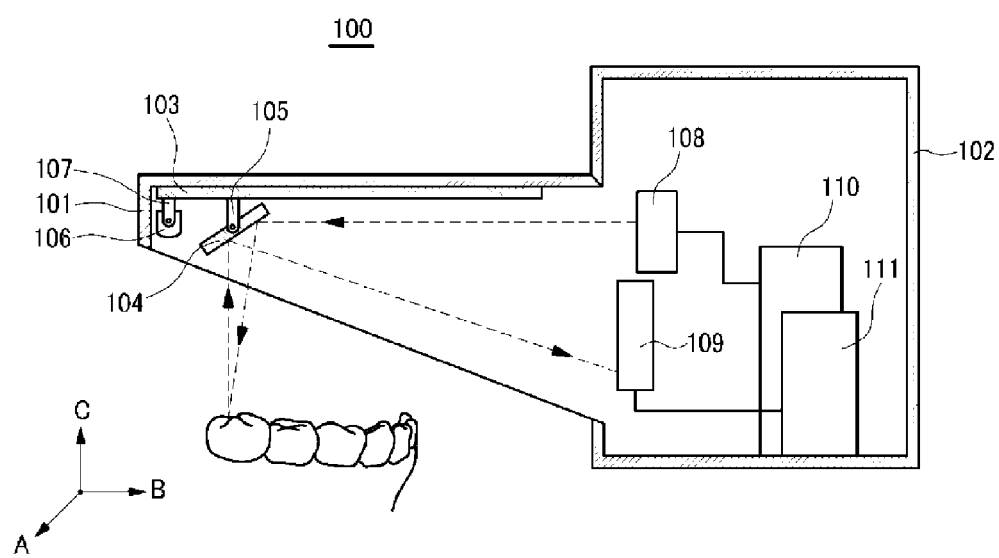
FIG. 2 is a side view of the oral cavity scanner in accordance with the first example embodiment.

FIG. 2 is a side view of the oral cavity scanner in accordance with the first example embodiment of the present disclosure.

As depicted in FIG. 1 and FIG. 2, an oral cavity scanner 100 in accordance with the first example embodiment includes an insertion body 101, a main body 102, a guide member 103, an optical system 104, an optical system driving unit 105, an imaging device 106, an imaging device driving unit 107, an optical output unit 108, an optical sensing unit 109, a control unit 110 and a data processing unit 111.

A frame of the insertion body 101 is in the form of an insertion tube protruded from the main body 102 so as to be insertable into oral cavity of a user. The insertion body 101 has five surfaces including a single top surface, two side surfaces, a single front surface (i.e., a front portion when inserted into the oral cavity) and a single bottom surface.

The bottom surface of the insertion body 101 is provided with a light transmitting window that allows a light source for scanning (in the present example embodiment, a line laser beam, for example) to be projected to a tooth therethrough, thus enabling the imaging device 106 to capture an image of an intraoral state.

The top surface of the insertion body 101 is parallel to a direction in which the insertion body is inserted into the oral cavity. The bottom surface is at a certain angle to the top surface. Accordingly, two side surfaces may be formed to be gradually enlarged toward the main body 102. This shape is designed to protect the light source by securing a traveling path of the light source output toward the optical system 104 through the inside of the insertion body 101 and a traveling path of the light source incident upon the light sensing unit 109 through the optical system 104 after reflected from the tooth. Meanwhile, besides the shape shown in FIG. 1 and FIG. 2, the insertion body 101 in accordance with the example embodiment may have various other shapes appropriately selected by users.

Within the insertion body 101, the optical system 104 is connected to the guide member 103 via the optical system driving unit 105. The optical system 104 is configured to reflect and project a line laser beam (hereinafter, referred to as "output light"), which is output from the optical output unit 108, to the tooth and, also, to reflect a beam (hereinafter, referred to as "incident light"), which arrives at the optical system 104 by being reflected from the tooth, to the optical sensing unit 103.

At this time, after the line laser beam output from the optical output unit 108 is irradiated to a target tooth to be scanned by being reflected through the optical system 104, it is then re-incident upon the optical system 104 by being reflected from the tooth. The laser beam having reached the optical system 104 is then projected to the optical sensing unit 109 by being reflected through the optical system 104.

The guide member 103 supports the optical system 104 such that the optical system 104 is mounted to the inside of the insertion body 101. Also, the guide member 103 guides the optical system 104 to be slid back and forth in a direction horizontal to the direction in which the insertion body 101 is inserted.

The optical system driving unit 105 is connected to the optical system 104 and is driven to allow the optical system 104 to be slid along the guide member 103. At this time, the optical system driving unit 104 is moved to a set position along the guide member 103 by being driving under the control of the control unit 110. The optical system driving unit 105 according to the example embodiment may be implemented by a rolling member configured to be rolled by a driving source (e.g., a motor).

The optical system driving unit 105 is also capable of changing a reflection angle of the output light by rotating the optical system 104 about a first reference axis under the control of the control unit 110. For reference, the first reference axis is coincident with an A-axis, as shown in FIG. 1, and at least two angles may be set as the reference angle. In this way, by changing the reflection angle of the optical system 104, sufficient incidence of output light and acquisition of reflection light can be achieved even for a shaded portion (e.g., between teeth and irregularities on surfaces of the teeth) where distortion of incidence and reflection of the light source may occur.

Within the insertion body 101, the imaging device 106 for capturing a two-dimensional image is connected to the guide member 103 via the imaging device driving unit 107.

For reference, the imaging device 106 in accordance with the example embodiment may be a COMS sensor or a solid state imaging device using a photodiode as a light receiving device and a charged coupled device (CCD) as a charge transfer device. The imaging device 106 outputs information upon light of image having passed through a lens as an electric signal.

Meanwhile, in FIG. 1 and FIG. 2, the imaging device 106 is shown to be located at a front portion farther away from the main body 102 than the optical system 105. However, the imaging device 106 may be located at a position closer to the main body 102 than the optical system 104 is.

At this time, the control unit 110 controls the imaging device 106 to capture a two-dimensional image from a position above the target tooth before or after the output light is projected to the target tooth through the optical system 104. Through this control, the output light reflected from the optical system 104 and the incident light reflected from the tooth can be prevented from being affected by light that may be generated when capturing the image of intraoral state.

Further, the imaging device driving unit 107 is capable of horizontally moving the imaging device 106 back and forth at the same time when the optical system 104 is horizontally moved back and forth, thus allowing the imaging device 106 to maintain a certain distance from the optical system 104.

Meanwhile, in FIG. 1 and FIG. 2, the imaging device 106 is illustrated as a separate member from the optical system 104. In an oral cavity scanner 100 in accordance with another example embodiment, however, the imaging device 106 and the optical system 104 may be provided as a single body. That is, as the position of the optical system 104 is moved, the position of the imaging device 106 is also moved. In case that the optical system 104 and the imaging device 106 are formed as a single body, the imaging device driving unit 107 may be omitted.

The optical output unit 108, the optical sensing unit 109, the control unit 110 and the data processing unit 111 are accommodated in the main body 102.

The optical output unit 108 is configured to output a light source (i.e., a line laser beam) toward the optical system 104. For reference, the optical output unit 108 may be implemented by a laser diode, and the optical output unit may have as small a size as possible to avoid scale-up.

Particularly, the optical output unit 108 according to the first example embodiment of the present disclosure is configured to output a line type light source and allows the line type light source to be irradiated to a target tooth to be scanned. That is, as the optical output unit 108 outputs a line laser beam as a scanning light source, scanning values for a single line on a tooth plane can be obtained concurrently through a single output of scanning light source. Thus, as compared to scanning using a point source, scanning velocity can be improved.

Besides, in case of the scanning using a point source, an additional driving unit for changing a position of the point source is required to irradiate the scanning light source to each position on the tooth plane. To elaborate, when using the point source as the scanning light source, the output light needs to be irradiated to all positions on the plane of the target tooth to be scanned by rotating the point source in a direction parallel to the A-axis or by moving the point source horizontally to the A-axis direction. In the present example embodiment, however, by using the line type light source as the scanning light source, an additional driving unit for setting the position of the optical output unit 108 is not needed. Thus, a space for accommodating the driving unit of the optical unit 108 and a space for allowing a movement of the optical output unit for the purpose of changing the position of the optical unit 108 need not be provided within the main body 102. Therefore, the oral cavity scanner 100 can be scaled down efficiently and, also, highly efficient component arrangement is possible.

For reference, in the present example embodiment, since the scanning of a single line on the plane of the target tooth to be scanned is performed whenever the optical output unit 108 outputs a line laser beam, coordinate values on a certain plane axis (i.e., the A-axis in FIG. 1 and FIG. 2) can be automatically calculated when performing a three-dimensional modeling of the tooth.

After the output light from the optical output unit 108 is reflected to the target tooth to be scanned through the optical system 104, the optical sensing unit 109 senses the light which is reflected again through the optical system 104 after reflected by the tooth. For reference, the optical sensing unit 109 in this example embodiment may be a light receiving device such as a charge coupled device (CCD) or a position sensitive device (PSD), but not limited thereto. In the present example embodiment, the optical sensing unit 109 is implemented by a PSD, for example. The PSD sensor is a photoelectron sensor and has an architecture whereby a photocurrent, which is proportionate to optic energy, is generated and flows to both ends of the sensor when a light spot is formed on a surface of the sensor.

To elaborate, the optical sensing unit 109 generates an electric signal according to a position to which the incident light (i.e., the line laser beam) is inputted, and sends the generated electric signal to the data processing unit 111.

The control unit 110 controls the operations of the optical system 104, the optical output unit 108 and the imaging device 106 individually, thus controlling three-dimensional scanning and two-dimensional imaging upon each portion of the target tooth and the teeth within the oral cavity. A configuration and an operation of the control unit 110 will be elaborate later with reference to FIG. 3.

The data processing unit 111 receives signals (or data) output from the optical sensing unit 109 and the imaging device 106, and generates and stores a three-dimensional model and a two-dimensional image of the target tooth based on the received signals. A configuration and an operation of the data processing unit 111 will be elaborated later with reference to FIG. 4.

Figure 3:
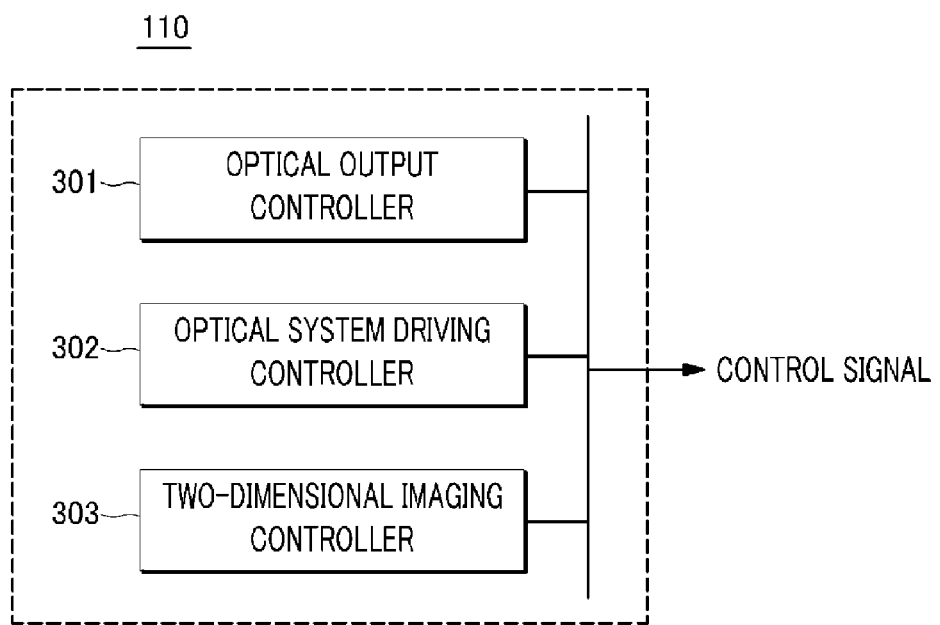
FIG. 3 is a block diagram illustrating a configuration of a control unit of the oral cavity scanner in accordance with the first example embodiment.

FIG. 3 is a block diagram illustrating a configuration of the control unit of the oral cavity scanner according to the first example embodiment of the present disclosure.

As depicted in FIG. 3, the control unit 110 includes an optical output controller 301, an optical system driving controller 302 and a two-dimensional imaging controller 303.

The optical output controller 301 controls the optical output unit 108 to output a line laser beam at a preset time point.

The optical system driving controller 302 controls the driving of the optical system driving unit 105 to change the reflection angle of the optical system 104 and move the optical system 104 to a required position. At this time, the optical system driving controller 302 allows the optical system driving unit 105 to be slid to a set position along the guide member 103 such that the optical system 104 is moved to a preset position. Further, the optical system driving controller 302 moves the optical system 104 back and forth horizontally by driving the optical system driving unit 105 depending on the position of the target tooth to be scanned.

Further, the optical system driving controller 302 may also control the optical system driving unit 105 to be rotated at a preset angle about the first reference axis. At this time, the optical system 104 is rotated by driving the optical system driving unit 105 at a rotation angle set to correspond to a target portion to be scanned.

To elaborate, the optical system driving controller 32 transmits information on the changed reflection angle to the data processing unit 111 whenever the reflection angle of the optical system 104 is changed. At this time, coordinate values of the scanning target tooth on a certain plane axis (i.e., a B-axis in FIG. 1 and FIG. 2) can be calculated based on a value of the rotation angle (i.e., the information on the reflection angle) controlled by the optical system driving control unit 302.

The two-dimensional imaging control unit 303 controls the imaging device 106 to capture a two-dimensional image of the target tooth to be scanned at a set time point. Further, the two-dimensional imaging control unit 303 controls the imaging device 107 to be slid to a set position along the guide member 103, thus allowing the imaging device 107 to capture the image of the target tooth within a certain distance from the optical system 104.

Figure 4:
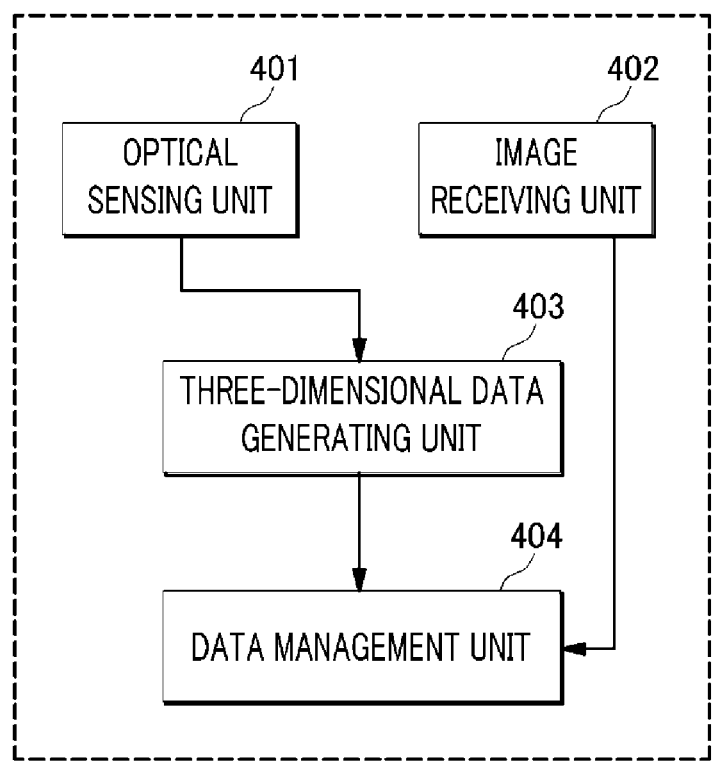
FIG. 4 is a block diagram illustrating a configuration of a data processing unit of the oral cavity scanner in accordance with the first example embodiment.

FIG. 4 is a block diagram illustrating a configuration of the data processing unit of the oral cavity scanner in accordance with the first example embodiment of the present disclosure.

As depicted in FIG. 4, the data processing unit 111 includes an optical sensing unit 401, an image receiving unit 402, a three-dimensional data generating unit 403 and a data management unit 404.

The optical sensing unit 401 generates position information (i.e., height values of respective portions of the target tooth) corresponding to electric signals output from the optical sensing unit 109 and sends the position information to the three-dimensional data generating unit 403. At this time, coordinate values of the scanning target tooth on a height axis (i.e., a C-axis in FIG. 1 and FIG. 2) can be calculated based on the height values (i.e., the position information according to the electric signals) generated by the optical sensing unit 401.

Here, the optical sensing unit 401 may calculate the coordinate values on the C-axis through displacement measurement using an optical triangulation method. The optical triangulation method is a technique of measuring a displacement by using two-dimensional triangulation based on geometric optics. In the optical triangulation method, the optical system is constructed with respect to two optical axes that exist on the same plane and cross each other at an angle of θ.

In this configuration, one of the two optical axes is a focusing axis for forming an optical spot on a surface of a measurement target, and the other is an imaging axis for projecting an image of the optical spot to the light receiving device. Here, the optical spot formed on the surface of the measurement target is moved straightly on the focusing axis as the relative position of the measurement target varies, and this moving range is referred to as an object trajectory. Further, as the optical spot is moved, an image point on the light receiving device is also moved, and this moving range of the image point is referred to as an image trajectory. The image trajectory has an angle of φ with respect to a vertical direction of the imaging axis.

At this time, a moving distance of the optical spot on the object trajectory and a moving distance q of the image point corresponding thereto can be calculated through the following Equation 1.

$$p = \frac{q\cos\phi(s-f)}{f\sin\theta + q\cos\phi\cos\theta} \quad \text{[Equation 1]}$$

For reference, f is a focal length of an image lens for projecting an image according to the optical spot to the light receiving device; and s denotes a distance between the image lens and an actual measurement target object Further, the angle ϕ can be calculated through the following Equation 2.

$$\phi = \tan^{-1}(f/(s-f)\tan\theta) \qquad \text{[Equation 2]}$$

If this optical triangulation method is applied to the example embodiment of the present disclosure, the output light forms an optical spot on the surface of the target tooth, and the reflected light from the target tooth (i.e., the incident light) forms an image on the PSD sensor. Then, the PSD sensor outputs an electric signal according to the image formation position of the incident light. At this time, since the position where the image is formed on the PSD sensor varies with the variation of the height of teeth, the height value of the target tooth can be calculated.

The image receiving unit 402 receives the two-dimensional image data of the target tooth sent from the imaging device 106 and, then, converts the received two-dimensional image data to a previously set format. Then, the image receiving unit 402 sends the converted image data to the data management unit 404.

The three-dimensional data generating unit 403 generates three-dimensional data by matching the A-axis coordinate values and the C-axis coordinate values received from the optical sensing unit 401 and the B-axis coordinate values received from the optical system driving control unit 302.

Here, the three-dimensional data generating unit 403 may output the generated three-dimensional data to an external apparatus (for example, a three-dimensional modeling apparatus) through the data management unit 404. Further, the three-dimensional data generating unit 403 may also be capable of performing three-dimensional modeling for the scanning target tooth and capable of storing it in connection with the two-dimensional image through the data management unit 404.

To elaborate, the three-dimensional data generating unit 403 generates a three-dimensional scanning model of the scanning target tooth by combining the mutually matched A-, B- and C-axis coordinate values among the generated three-dimensional data.

For reference, the entire processing unit 111 or some of its components may be incorporated within the oral cavity scanner 100 or may be connected to the oral cavity scanner through a cable or the like as a separate apparatus. In FIG. 1 and FIG. 2, the data processing unit 111 is shown to be included in the main body of the oral cavity scanner 100, and the three-dimensional data generating unit 403 is shown to be incorporated in the data processing unit 111. However, to limit the size of the oral cavity scanner, a part of or the entire configuration of the data processing unit 111 may be provided outside the oral cavity scanner.

The data management unit 404 stores therein the two-dimensional image of the scanning target tooth received from the image receiving unit 402 and the three-dimensional data (or three-dimensional model) received from the three-dimensional data generating unit 403 by matching them with each other.

At this time, the data management unit 404 may store the three-dimensional data (or three-dimensional model) of the scanning target tooth and the two-dimensional image matched thereto in a storage medium (for example, a database) in sequence.

For reference, the data management unit 404 may transmit the matched three-dimensional data and two-dimensional image data to the external apparatus.

Further, the data management unit 404 may output the three-dimensional scanning model and the two-dimensional image of the patient's tooth stored therein through an output device (screen) (not shown), an output system (not shown) connected to a data cable or a network, or the like.

As stated above, by storing and outputting the three-dimensional scanning model of the target tooth in connection with the two-dimensional image matched thereto, it is possible to correct and investigate the three-dimensional scanning model without needing to directly check the patient's affected area. Further, a user can perform the scanning operation for the tooth while checking the two-dimensional image data being captured in a real time.

Meanwhile, the oral cavity scanner 100 may be scaled down to be more conveniently used. Accordingly, the respective components (i.e., the optical output unit, the optical sensing unit, the control unit and the data processing unit) accommodated in the oral cavity scanner 100 may be densely arranged in order to improve efficiency in space utilization.

Accordingly, in order to secure a traveling path of a line laser beam output from the optical output unit 108 of the oral cavity scanner, oral cavity scanners 100 according to other example embodiments may be configured to allow a line laser beam output from the optical output unit 108 to reach the optical system 104 after changing the traveling path of the line laser beam, unlike the oral cavity scanner according to the first example embodiment described above with reference to FIG. 1 to FIG. 4.

Below, oral cavity scanners in accordance with other example embodiments which are configured to allow a line laser beam to reach an optical system after a traveling path of the line laser beam is changed will be discussed with reference to FIG. 5 to FIG. 8. For reference, in FIG. 5 to FIG. 8, detailed description of the same parts as those of the oral cavity scanner 100 according to the above-described first example embodiment will be omitted for the simplicity of explanation.

Figure 5:
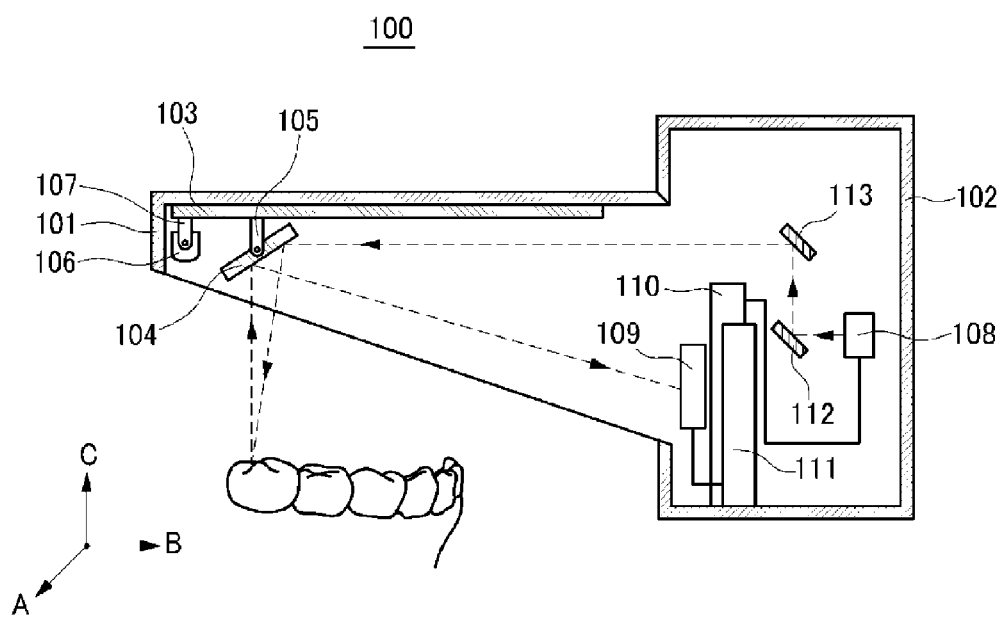
FIG. 5 is a side view of an oral cavity scanner in accordance with a second example embodiment of the present disclosure.
Figure 6:
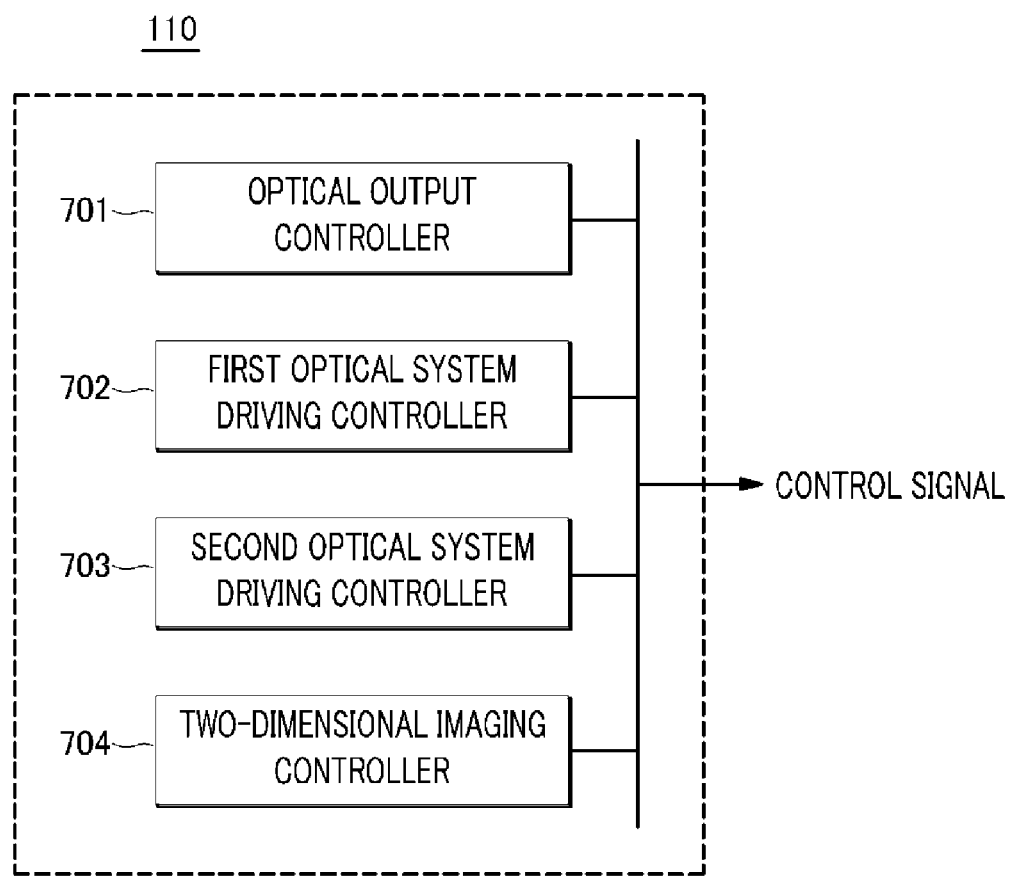
FIG. 6 is a block diagram illustrating a configuration of a control unit of an oral cavity scanner in accordance with the second example embodiment.

FIG. 5 is a side view of an oral cavity scanner in accordance with a second example embodiment. FIG. 6 is a block diagram illustrating a configuration of a control unit of the oral cavity scanner in accordance with the second example embodiment.

As depicted in FIG. 5, the oral cavity scanner 100 according to the second example embodiment includes, within an insertion body 101, a guide member 103, a first optical system 104, an optical system driving unit 105, an imaging device 106 and an imaging device driving unit 107. Further, the oral cavity scanner 100 also includes, within a main body 102, an optical output unit 108, a second optical system 112, a third optical system 113, an optical sensing unit 109, a control unit 110 and a data processing unit 111.

Here, as illustrated in FIG. 5, other components (i.e., the optical sensing unit, the control unit, the data processing unit, etc.) are provided in front of the optical output unit 104 in a direction of the insertion body. Accordingly, to secure a traveling path of a line laser beam output from the optical output unit 108, the second optical system 112 and the third optical system 113 are provided. For reference, although FIG. 5 illustrates a configuration where the two optical systems for changing the optical path are provided in the oral cavity scanner 100 according to the second example embodiment, optical systems for changing the optical path may be provided at two or more positions depending on positions of the components within the main body 102 and a traveling path of the output light from the optical system 108.

To elaborate, as depicted in FIG. 5, a line laser beam output from the optical system 108 is reflected in a vertical direction (i.e., an upward direction on a C-axis in FIG. 5) through the second optical system 112. Then, the line laser beam reflected by the second optical system 112 is reflected again by the third optical system 113 and outputted in an initial traveling direction (i.e., in a direction toward the first optical system on a B-axis in FIG. 5). Then, the operation of the oral cavity scanner 100 after the incidence of the output light (i.e., the line laser beam) upon the first optical system 104 is the same as stated above.

In FIG. 5, the line laser beam output from the optical output unit 108 in a first traveling direction is reflected by the second optical system 112, whereby its traveling direction is changed to a second traveling direction which is different from the first traveling direction. Then, the line laser beam traveling in the second traveling direction is reflected by the third optical system 113 again to the original first traveling direction. For reference, the oral cavity scanner in accordance with the second example embodiment may include at least two optical systems for changing the optical path. Accordingly, the scanning light source output from the optical output unit 108 may change the traveling path at least two times.

For reference, in FIG. 5, reflection angles and positions of the second and third optical systems 112 and 113 are fixed, and a driving unit for varying the reflection angles or positions is not provided. In accordance with still another example embodiment, however, a second and a third driving unit (not shown) may be provided, and the second and third driving units may be operated under the control of the controller 110.

As depicted in FIG. 6, the control unit 110 of the oral cavity scanner 100 in accordance with the second example embodiment of the present disclosure includes an optical output controller 701, a first optical system driving controller 702, a second optical system driving controller 703 and a two-dimensional imaging controller 701.

In this configuration, the second optical system driving controller 703 according to the second example embodiment controls driving units (not shown) of the first and second optical systems 112 and 113, thus adjusting the positions or reflection angles of the second and third optical systems 112 and 113. Accordingly, it is possible to adjust the traveling path of the line laser beam output from the optical output unit 108 precisely, and even if the positions of the other components within the main body 102 are varied, the output path of the line laser beam can still be secured.

The optical output controller 701, the first optical system driving controller 702 and the two-dimensional imaging controller 704 perform the same or similar operations as those of the optical output controller 301, the optical system driving controller 302 and the two-dimensional image capturing controller 303 described in FIG. 3, respectively. For reference, the optical output controller 701 performs the same or similar control operation as that of the optical output controller 301 described in FIG. 3. However, the optical output controller 701 may further control a line laser beam to be output at an appropriate time point in consideration of a change of the traveling path of the output light.

Figure 7:
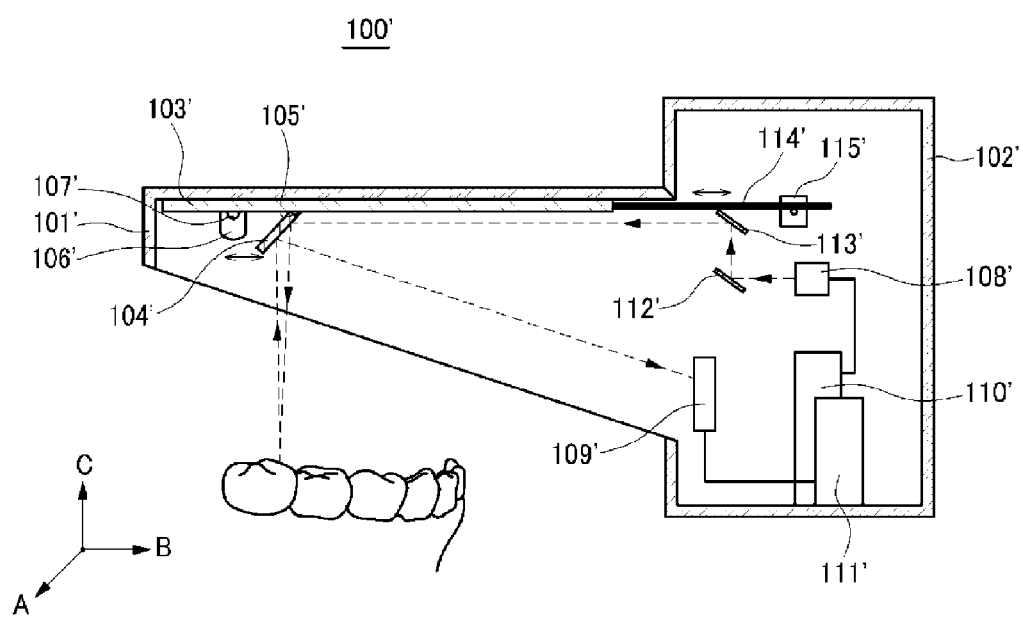
FIG. 7 is a side view of an oral cavity scanner in accordance with a third example embodiment of the present disclosure.
Figure 8A:
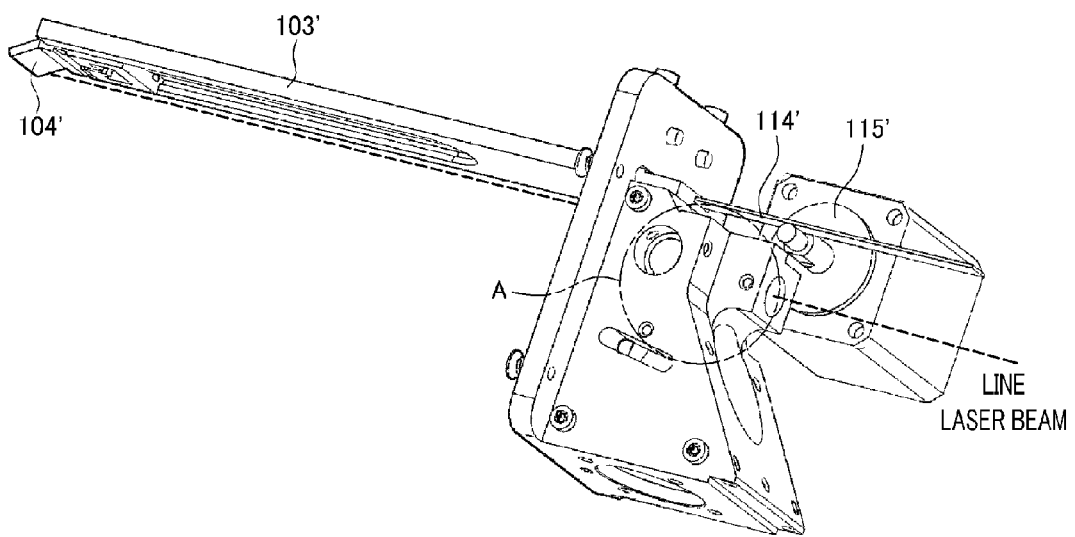
FIG. 8A provides three-dimensional views illustrating a part of the oral cavity scanner in accordance with the third example embodiment.
Figure 8B:
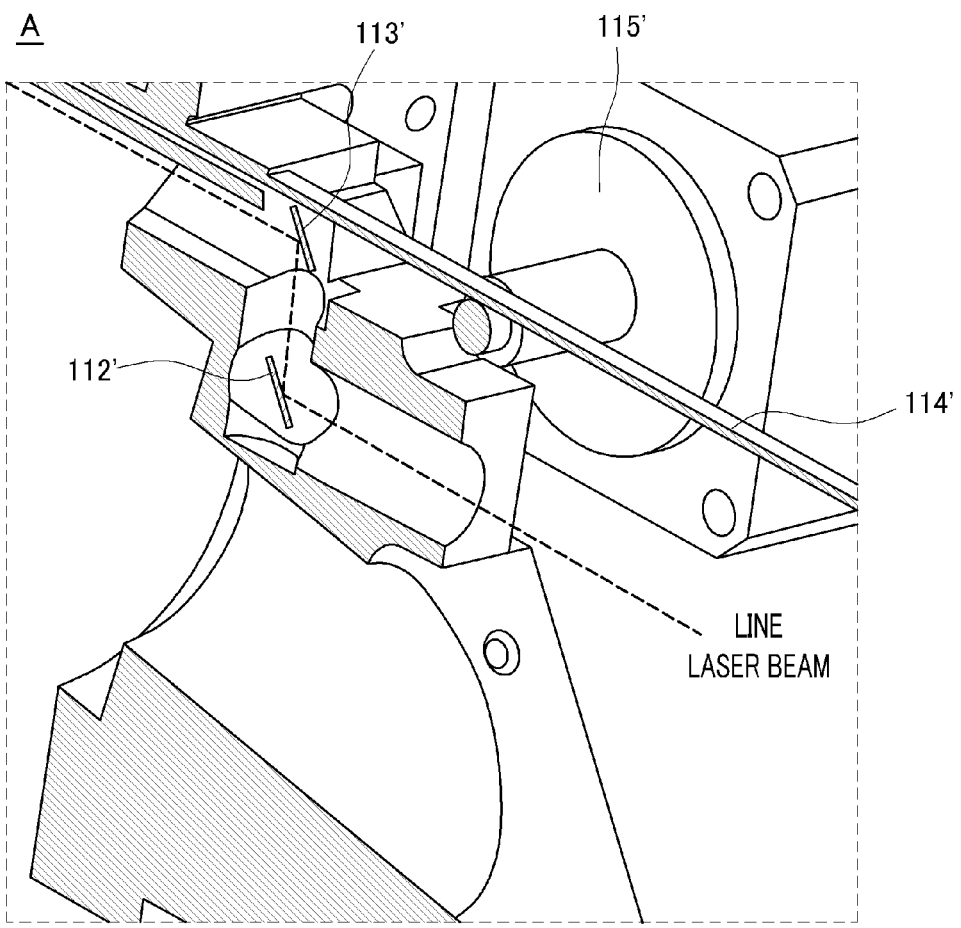
FIG. 8B provides three-dimensional views illustrating a part of the oral cavity scanner in accordance with the third example embodiment.

FIG. 7 is a side view of an oral cavity scanner in accordance with a third example embodiment of the present disclosure, and FIG. 8A and FIG. 8B provide three-dimensional views of a part of the oral cavity scanner in accordance with the third example embodiment.

As shown in FIG. 7, an oral cavity scanner 100' in accordance with the third example embodiment includes an insertion body 101', a main body 102', a guide member 103', a first optical system 104', a first optical system driving unit 105', an imaging device 106', an imaging device driving unit 107', an optical output unit 108', an optical sensing unit 109', a control unit 110', a data processing unit 111', a second optical system 112', a third optical system 113', a sliding bar 114' for moving the optical system 104' and the optical system driving unit 105', and a sliding bar driving unit 115' configured to operate the sliding bar 114'. For reference, the individual components (i.e., the individual parts) of the oral cavity scanner 100' correspond to the components (i.e., the individual parts) of the oral cavity scanner 100 as described above with reference to FIG. 1 to FIG. 6, detailed description of operations of corresponding parts will be omitted for the simplicity of explanation.

The optical system driving unit 105' and the imaging device driving unit 107' of the oral cavity scanner 100' according to the third example embodiment connect the optical system 104' and the imaging device 106' to the sliding bar 114'. Thus, the positions of the optical system 104' and the imaging device 106' are changed as the position of the sliding bar 114' is moved.

To elaborate, as shown in FIG. 8A, as the sliding bar 114' of the oral cavity scanner 100' is slid along the guide member 103', the position of the first optical system 104' connected to the sliding bar 114' is moved forward or backward. At this time, the sliding bar driving unit 115' may be composed of a driving motor including a rolling member in contact with the sliding bard 114' and configured to roll the sliding bar 114 so that the sliding bar 114' makes a sliding motion. For example, the driving motor may be provided as one body with the rolling member or coupled thereto. For reference, in FIG. 8A, the imaging device 106' and the imaging device driving unit 107' are omitted for the simplicity of illustration. Further, the first optical system 104' may be connected to the sliding bar 114' through the first optical system driving unit 105'.

Referring back to FIG. 7, it may be difficult to secure a traveling path of a line laser beam within the main body 104' due to the volume of the sliding bar driving unit 115' provided within the main body 104' and the sliding movement of the sliding bar 114'.

For example, as in the first example embodiment described in FIG. 1 and FIG. 2, if the optical output unit 108 is positioned in alignment with the optical system 104, at least a part of the sliding bar 114' and the sliding bar driving unit 115' according to the third example embodiment may be located between the optical output unit 108 and the optical system 104, thus blocking a traveling path of a line laser beam. That is, the sliding bar 114' is moved forward and backward along the guide member 103', and if a space for the forward and backward movements of the sliding bar 114' is secured, it may be difficult to secure the traveling path of the line laser beam of the optical output unit 108.

To solve the problem, as shown in FIG. 7, in the oral cavity scanner 100' according to the third example embodiment of the present disclosure, the optical output unit 108' may be provided at a position spaced apart from a moving path of the sliding bar 114' within the main body 102'. In this configuration, as shown in FIG. 8B, a laser beam output from the optical output unit 108' in a first traveling direction may be made to change its traveling direction to a second traveling direction, which is different from the first traveling direction, by being reflected by the second optical system 112'. Then, the line laser beam may be reflected again by the third optical system 113' and made to proceed in the original first traveling direction to reach the optical system 104'. In this way, the optical path for the incidence of the line laser beam upon the optical system 104' is secured.

In the above description, each of the constituent components shown in FIG. 3, FIG. 4 and FIG. 6 according to the example embodiments of the present disclosure may imply software or hardware such as a field programmable gate array (FPGA) or an application specific integrated circuit (ASIC), and they carry out predetermined functions.

However, the components are not limited to the software or the hardware, and each of the components may be stored in an addressable storage medium or may be configured to implement one or more processors.

Accordingly, the components may include, for example, software, object-oriented software, classes, tasks, processes, functions, attributes, procedures, sub-routines, segments of program codes, drivers, firmware, micro codes, circuits, data, database, data structures, tables, arrays, variables and the like.

The components and functions thereof can be combined with each other or can be divided.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

We claim:

1. An oral cavity scanner, comprising:
an optical output unit configured to output a line laser beam;
a second optical system configured to reflect the line laser beam, which is output from the optical output unit in a first traveling direction, in a second traveling direction different from the first traveling direction;
a third optical system configured to reflect the line laser beam, which is reflected from the second optical system, in the first traveling direction;
a first optical system configured to reflect the line laser beam output from third optical system to a scanning target tooth;
an optical sensing unit configured to sense the line laser beam reflected again by the first optical system after reflected from the scanning target tooth;
a main body in which the optical output unit, the optical sensing unit and the control unit are accommodated;
an insertion body protruded from the main body so as to be inserted into oral cavity, and accommodating therein the first optical system;
a first optical system driving unit provided within the insertion body and configured to slide the first optical system in a forward or backward direction horizontal to an insertion direction of the insertion body into the oral cavity;
a guide member provided within the insertion body and configured to guide the first optical system driving unit to be slid in the forward or backward direction; and
a control unit configured to control operations of the optical output unit, the first optical system, the second optical system, the third optical system, the first optical system driving unit and guide member;
wherein the control unit controls a reflection angle and a position of the first optical system and
wherein the line laser beam reflected from the third optical system is reflected to the scanning target tooth through the first optical system.

2. The oral cavity scanner of claim 1, further comprising:
a data processing unit configured to generate three-dimensional data for generating a three-dimensional model of the scanning target tooth based on sensing values output from the optical sensing unit and a value of the reflection angle of the first optical system.

3. The oral cavity scanner of claim 2,
wherein the data processing unit generates coordinate data of the scanning target tooth on a plane A-axis based on the value of the reflection angle of the first optical system, and generates height value data for each coordinate of a B-axis line perpendicular to the A-axis.

4. The oral cavity scanner of claim 1, further comprising:
a two-dimensional imaging device configured to capture a two-dimensional image of the scanning target tooth.

5. The oral cavity scanner of claim 4,
wherein the control unit controls the two-dimensional imaging device to capture the two-dimensional image of the scanning target tooth before or after the optical output unit outputs the line laser beam.

6. The oral cavity scanner of claim 4, further comprising:
a data processing unit configured to generate the three-dimensional data for generating the three-dimensional model of the scanning target tooth based on values of electric signals output from the optical sensing unit and the value of the reflection angle of the first optical system, and store the two-dimensional image output from the two-dimensional imaging device while matching the two-dimensional image with the three-dimensional data.

7. The oral cavity scanner of claim 1,
wherein the insertion body is provided with, at one side thereof, a light transmitting window through which the line laser beam reflected by the first optical system is irradiated to the scanning target tooth.

* * * * *